United States Patent [19]

Bloodworth et al.

[11] Patent Number: 5,171,476

[45] Date of Patent: Dec. 15, 1992

[54] PREPARATION OF EMULSIONS OR OTHER MULTIPHASE FORMULATIONS

[75] Inventors: Robert Bloodworth, Cologne; Günther Penners, Leverkusen; Wolfgang Podszun, Cologne; Jürgen Reiners, Leverkusen; Hans Schulze, Cologne, all of Fed. Rep. of Germany

[73] Assignee: Bayer Aktiengesellschaft, Leverkusen, Fed. Rep. of Germany

[21] Appl. No.: 570,253

[22] Filed: Aug. 20, 1990

[30] Foreign Application Priority Data

Sep. 8, 1989 [DE] Fed. Rep. of Germany ....... 3929866

[51] Int. Cl.$^5$ ............................................. B01J 13/00
[52] U.S. Cl. ................... 252/314; 252/8.554; 252/8.9; 252/312; 252/351; 252/DIG. 1; 556/465; 556/471; 556/482
[58] Field of Search ................. 252/357, DIG. 1, 312, 252/314; 556/465, 471, 482

[56] References Cited

U.S. PATENT DOCUMENTS

| | | | |
|---|---|---|---|
| 2,917,480 | 12/1959 | Bailey et al. | 252/351 X |
| 3,308,149 | 3/1967 | Schenck et al. | 556/482 X |
| 3,359,212 | 12/1967 | Bailey et al. | 252/351 X |
| 3,600,418 | 8/1971 | Bailey et al. | 252/351 X |
| 4,060,538 | 11/1977 | Kötzsch et al. | 556/471 X |
| 4,160,776 | 7/1979 | Scardera | 556/446 |
| 4,226,794 | 10/1980 | Scardera et al. | 252/351 X |
| 4,306,035 | 12/1981 | Baskent et al. | 252/DIG. 1 |
| 4,698,178 | 10/1987 | Hüttinger et al. | 252/351 X |

OTHER PUBLICATIONS

Synthesis, Nr. 3, Mar. 1977, pp. 184–186; H. Lehmkuhl et al.
Chemical Abstracts, Band 83, 1975, p. 241, 62401d.
Chemical Abstracts, Band 82, 1975, p. 181, 60453c.
Chemical Abstracts, Band 83, 1975, p. 268, 118483b.

*Primary Examiner*—Richard D. Lovering
*Attorney, Agent, or Firm*—Sprung Horn Kramer & Woods

[57] ABSTRACT

The invention relates to new cleavable surface-active silane derivatives of the formula $$R_1-O+CH_2-CH_2-O\overline{)_n}Si+X\overline{)_m}R_4, \quad (I)$$

with $R_2$ and $R_3$ substituents on Si in which $R_1$, n, $R_2$, $R_3$, X, m and $R_4$ have the meaning given in the description, and furthermore processes for the preparation of these silane derivatives and the use of these compounds as surfactants.

1 Claim, No Drawings

PREPARATION OF EMULSIONS OR OTHER MULTIPHASE FORMULATIONS

The invention relates to new cleavable surface-active compounds (surfactants), processes for their preparation and their use for the preparation of emulsions or other multi-phase formulations.

Surfactants are compounds in which the molecules are built up from hydrophilic and hydrophobic parts. Because of their amphiphilic character, these compounds are surface-active and become enriched at the interface between an aqueous phase and a hydrophobic phase. The hydrophobic phase can be a gas, a liquid or a solid. On enrichment, the surfactants form monomolecular films at the interfaces, which means that the properties of the systems are decidedly influenced, which may lead both to desirable and to undesirable effects.

When classifying surfactants according to their hydrophobic groups, a distinction is made between those having hydrocarbon groups, those having partly fluorinated or perfluorinated hydrophobic radicals and those based on siloxane or polyester.

When classifying them according to hydrophilic groups, a distinction is made between anionic surfactants, the hydrophilic parts of which are formed by anions of the acids of phosphorus or sulphur or of carboxylic acids, cationic surfactants having quaternized nitrogen functions and nonionic surfactants, the hydrophilic groups of which are formed by polyethyleneglycol ethers or polyalcohols.

All these known surfactants have the common feature that they only lose their surface-active properties by biological degradation, by non-specific chemical destruction or, in the case of anionic surfactants, by complexing, for example with $Ca^{++}$ or $Al^{+++}$. In recent years, however, very interesting possible uses for surfactants have been found, but these require that the surfactants, immediately after they have fulfilled their purpose, are split in the reaction medium into fragments which are no longer surface-active, for example by a change in the pH, and in this way lose their surface-active effect (see (a) J. Org. Chem. 1982, 47, 311-315; (b) 1982, 47, 2221-2223; and (c) 1984, 49, 4545-4547). Cleavable cationic surfactants are described in (a), (b) and (c), and in particular cationic surfactants having ketal groups are proposed in (a) and (b) for use in neutral and basic media; however, these have the disadvantage that they are cleavable only under drastic conditions (at pH values <1), for example with the aid of 5% strength hydrochloric acid. Cationic surfactants which contain monoalkoxysilane units and likewise are cleavable only under drastic conditions (at pH values <1 or >12) are described in (c).

The cleavable surfactants known to date have the disadvantage that on the one hand they can be cleaved only under drastic conditions, that is to say at pH values <1 and >12, and moreover are cationic. In practice, however, nonionic surfactants are required because they are more universally applicable and have a lower sensitivity towards electrolytes, and in particular those nonionic surfactants which are already split under mild conditions, for example at pH values >1 and <11.

Surprisingly, it has been found that silane derivatives of a certain structure have these desired properties.

The invention therefore relates to silane derivatives of the formula

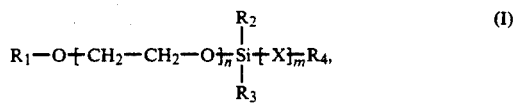

in which
$R_1$ denotes H or $C_1$–$C_4$-alkyl,
n denotes an integer from 2 to 300,
$R_2$ and $R_3$ independently of one another denote $C_1$–$C_{16}$-alkyl or phenyl,
X denotes —O—, —S—, —$NR_5$—($R_5$: hydrogen or $C_1$–$C_4$-alkyl) or

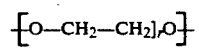

(r = integer from 1 to 100) and
m denotes zero or 1, and
$R_4$ denotes H, $C_1$–$C_{36}$-alkyl, $C_2$–$C_{36}$-alkenyl, $C_5$–$C_{36}$-cycloalk(en)yl, $C_7$–$C_{36}$-aralkyl, $C_6$–$C_{36}$-aryl, a radical of the formula (II)

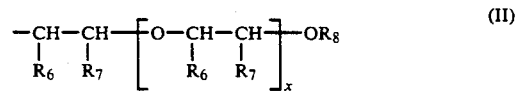

in which one of the radicals $R_6$ and $R_7$ represents methyl and the other represents H, $R_8$ denotes $C_1$–$C_4$-alkyl and x represents an integer from 10 to 300, or a radical of the formula (III)

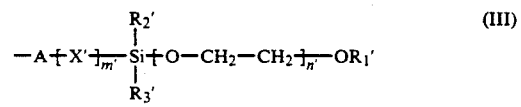

in which
$R_1'$, $R_2'$, $R_3'$, $X'$, $m'$ and $n'$ have the meanings given for $R_1$, $R_2$, $R_3$, X, m and n under formula (I) and
A represents a 2-valent hydrophobic radical, for example an alk(en)ylene, oxaalkylene, cycloalk(en)ylene, alkarylene or aryl-alkylene radical containing at least 12C atoms, with the proviso that the sum of the C atoms contained in the radicals $R_2$, $R_3$ and $R_4$ is at least 14.

Examples which may be mentioned of representatives of the radicals mentioned for $R^4$ are: $C_1$–$C_{36}$-alkyl radicals, such as the methyl, ethyl, n- and i-propyl, n- and sec-butyl-, 2-ethylhexyl, n-decyl-n-dodecyl-, hexadecyl-, octadecyl- and behenyl($C_{22}$) radical; $C_2$–$C_{36}$-alkenyl radicals, such as the propenyl, butenyl, hexenyl, octenyl, hexadecenyl and octadecenyl radical; $C_5$–$C_{36}$-cycloalk(en)yl radicals, such as the cyclopentyl, cyclohexyl and cyclopentadienyl radical, and cyclohexyl radicals substituted by alkyl groups, such as the methylcyclohexyl, dimethylcyclohexyl and tert.-butylcyclohexyl radical; $C_7$–$C_{36}$-aralkyl radicals, such as the benzyl and the β-phenylethyl radical, and benzyl radicals substituted by alkyl groups, such as the methyl-benzyl, nonyl-benzyl and the dodecyl-benzyl radical; and $C_6$–$C_{36}$-aryl radicals, such as the phenyl, 4-octyl-phenyl, 4-nonyl-phenyl and 4-dodecyl-phenyl radical.

Examples which may be mentioned of representatives of the 2-valent hydrophobic radicals mentioned for A containing at least 12C atoms are:
$C_{12}$–$C_{36}$-alkylene radicals, such as the dodecylene, hexadecylene and octadecylene radical;

$C_6$–$C_{36}$-alkenylene radicals, such as the hexadecenylene and octadecenylene radicals, hydrophobic oxaalkylene radicals, for example poly-(1-methyl-3-oxa)-propylene radicals of the formulae

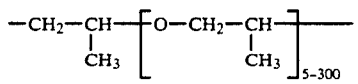

preferably

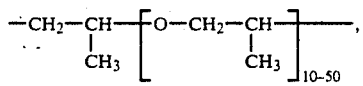

and alkylene-poly-(1-methyl-3-oxy-)propylene radicals of the formulae

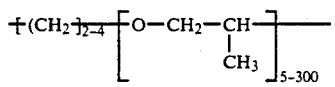

for example

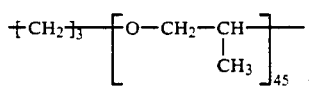

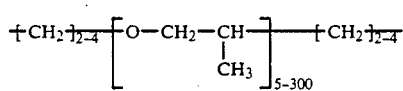

for example

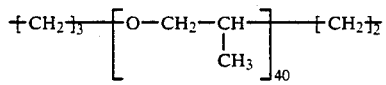

$C_{12}$–$C_{36}$-cycloalk(en)ylene radicals, such as the cyclohexylene, methylcyclohexylene, cyclohexenylene and the dicyclopentadienedimethylene radical.

Examples which may be mentioned of representatives of the $C_1$–$C_{16}$-alkyl radicals mentioned for $R^2$ and $R^3$ are: the methyl, ethyl, n- and sec.-butyl-, i-pentyl, n-hexyl, n-decyl, undecyl-, dodecyl-, tridecyl- and hexadecyl radical.

The silane derivatives of the formula (I) are preferred if, in these derivatives, $R_1$ denotes $C_1$–$C_4$-alkyl, n denotes an integer from 5 to 50, $R_2$ and $R_3$ independently of one another denote $C_1$–$C_{16}$-alkyl or phenyl, X denotes —O—, —S—, —$NR_5$— ($R_5$: hydrogen or $C_1$–$C_4$—alkyl) or

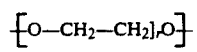

(r: integer from 5 to 50) and m denotes 0 or 1, and $R_4$ represents $C_1$–$C_{20}$-alkyl, $C_2$–$C_{20}$-alkenyl, $C_7$–$C_{20}$-aralkyl or $C_6$–$C_{20}$-aryl, or represents a radical of the formula

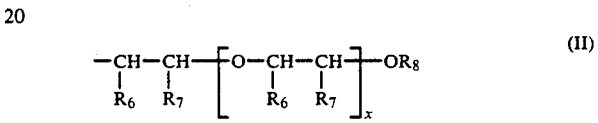

(II)

in which one of the radicals $R_6$ and $R_7$ represents methyl and the other represents H, $R_8$ is $C_1$–$C_4$-alkyl and x represents an integer from 10 to 50.

The silane derivatives of the formula (I) are particularly preferred if, in these derivatives, $R_1$ denotes methyl or ethyl, n denotes an integer from 5 to 50

$R_2$ and $R_3$ independently of one another denote for $C_1$–$C_{16}$-alkyl or phenyl, X denotes —O—, —S—, —NH— or —O—$CH_2CH_2]_rO$, where r = n, m denotes 1 and $R_4$ denotes $C_8$–$C_{20}$-alkyl, $C_8$–$C_{20}$-aralkyl or $C_6$–$C_{20}$-aryl, or $R_4=R_1$.

The compounds listed in the following table I may be mentioned as examples of representatives of the cleavable silane derivatives of the formula (I) according to the invention; the preparation of the compounds 1–13 is described in Examples 1–13.

TABLE 1

| Preparation described in Example | Silane derivatives according to the invention formula (I) |
|---|---|
| 1, 2 and 3 | $CH_3O{+}CH_2{-}CH_2{-}O{\rightarrow}_n Si(CH_3)(CH_3){-}O{-}C_{12}H_{25}$<br>n = 10, 16, 30 |
| 4, 5, 6 and 7 | $CH_3O{+}CH_2{-}CH_2{-}O{\rightarrow}_n Si(CH_3)(CH_3){-}O{-}\text{C}_6\text{H}_4{-}C_9H_{19}$<br>n = 10, 16, 30, 45 |
| 8 | $CH_3O{+}CH_2{-}CH_2{-}O{\rightarrow}_{30} Si(CH_3)(CH_3){+}O{-}CH_2CH_2{\rightarrow}_{12}O{-}\text{C}_6\text{H}_4{-}C_9H_{19}$ |

TABLE 1-continued

| Preparation described in Example | Silane derivatives according to the invention formula (I) |
|---|---|
| 9 | |
| 10 and 11 | |
| 12 and 13 | |
| | |
| | |
| 14-18 | |

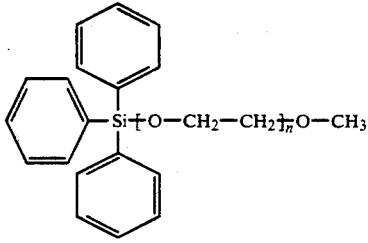

The surfactants according to the invention are distinguished by an excellent emulsifier action in the pH range from 5 to 10; the emulsions prepared with these are stable for weeks in this pH range. In contrast, outside this pH range the surfactants according to the invention are rapidly cleaved into surface-inactive fragments. The emulsions prepared with these surfactants therefore break down outside the pH range of 5-10 into their aqueous and hydrophobic phases. The surfactants according to the invention are therefore particularly suitable as emulsifiers for the treatment of textiles and fibres, for metalworking and for oil recovery.

The invention furthermore relates to the processes for the preparation of the silane derivatives of the formula (I) according to the invention. The silane derivatives of the formula (I) are obtained—in the case where $m=1$—by a process in which silanes of the formula (V)

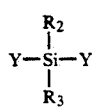 (V)

in which
$R_2$ and $R_3$ have the meaning given under formula (I) and Y denotes a hydrolysable atom or a hydrolysable group, are first reacted either with compounds containing reactive hydrogen, of the formulae $$R_1-O-[CH_2CH_2-O]_nH \qquad (VI),$$

in which $R^1$ and n have the meaning given under formula (I), or $$R_4-X-H \qquad (VII)$$

in which $R_4$ and X have the meaning given under formula (I), to give silane compounds of the formulae

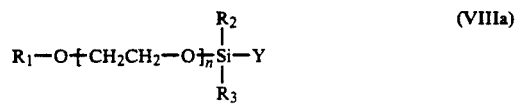 (VIIIa)

or

-continued

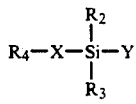
(VIIIb)

in which $R_1$, $R_2$, $R_3$, $R_4$, n and X have the meaning given under formula (I) and Y has the meaning given under formula (V); and these silane compounds (VIIIa) or (VIIIb) are then reacted again in a second reaction stage with the compounds of the formulae (VII) or (VI), and in particular the silane compounds (VIIIa) are reacted with the compounds of the formula (VII) and the silane compounds (VIIIb) are reacted with the compounds of the formula (VI).

The silane compounds of the formula (I) are obtained in a particularly simple manner if, in these compounds, m is 1, X is —[OCH$_2$CH$_2$]$_r$—O— (where r=n) and $R_4$ is $R_1$, that is to say if the radical X—$R_4$ is $R_1$O—[CH$_2$CH$_2$—O]$_n$. These compounds are obtainable in a single-stage reaction of the compound (V) with 2 mol of the compound of the formula (VI). It is also possible to use mixtures of various compounds of the formula (V) instead of one compound of the formula (V).

The silane derivatives of the formula (I) according to the invention, if m is 0 in these, are obtained by reaction of silanes of the formula (IX)

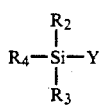
(IX)

in which $R_2$, $R_3$ and $R_4$ have the meaning given under formula (I) and Y has the meaning given under formula (V), with compounds containing reactive hydrogen, of the formula (VI).

Examples which may be mentioned of Y as a group which can be split off hydrolytically are alkoxy groups, such as methoxy or ethoxy groups, or carboxylate groups and pseudo-halides, such as cyanide groups or thiocyanate groups, and as atoms which can be split off by hydrolysis halogen atoms, preferably Cl and bromine atoms.

The reactions of the silanes of the formulae (V), (VIIIa), (VIIIb) and (IX) are carried out in an inert gas atmosphere in organic solvents which are inert under the reaction conditions and in the presence of bases at temperatures of 0°-100° C.

The silanes of the formula (V) are reacted with the compounds containing reactive hydrogen in a molar ratio of 3-6:1, and the silanes of the formulae (VIIIa), (VIIIb) and (IX) are reacted in a molar ratio of 1:1.

Tertiary amines, for example triethylamine and pyridine, have proved to be particularly suitable bases.

Examples which may be mentioned of organic solvents which are inert under the reaction conditions are aliphatic, cycloaliphatic and aromatic hydrocarbons; cyclohexane, benzene and toluene have proved to be particularly suitable. The solvents are preferably employed in an amount such that the weight ratio of reactants: solvent is 1:1 to 1:20.

The bases are preferably employed in excess, based on the amount of hydrolysable groups or atoms to be split off. If tertiary amines are used, the ammonium salts which are particularly easy to separate off are formed and the excess amine can be removed by distillation after the reaction. Molar ratios of tertiary amine/hydrolysable groups (atoms) to be split off of 1.05-1.1:1 have proved to be particularly suitable.

The conversion in the reaction can be monitored in a simple manner by a quantitative determination of the ammonium salt formed. When the reaction has ended, the ammonium salt can be separated off by filtration and the surfactant according to the invention can be isolated by removal of the solvent.

The starting compounds (V), (VI), (VII) and (IX) required for the preparation of the silane derivatives of the formula (I) according to the invention are either commercially available or can be prepared by reactions which are known per se (see, for example, Houben-Weyl Methoden der organischen Chemie [Methods of organic chemistry], 4th edition, volume 13/5, page 106, volume E 20, page 1367).

The invention furthermore relates to the use of the silane derivatives of the formula (I) according to the invention as surfactant.

EXAMPLES

EXAMPLES 1-9

(A) Preparation of the silane compounds of the formual (VIIIa) (general procedure)

To 5 mol of dichlorodimethylsilane in a reaction vessel filled with dry nitrogen there are added simultaneously a) a 50% strength by volume solution of one mol of a compound containing reactive hydrogen (compound of formula (VII)) in anhydrous toluene and b) a 50% strength by volume solution of 1.05 mol of triethylamine in anhydrous toluene at 30° C., while stirring. The reaction mixture is heated to 70° C. and stirred at this temperature for 2 hours. The ammonium salt precipitate is then filtered off with suction and the filtrate is freed from the solvent and excess dichlorodimethylsilane by vacuum distillation.

(B) Preparation of the silane derivatives of the formula (I) according to the invention A 50% strength by volume solution of a compound of the formula (VII) in dry toluene and a 50% strength by volume solution of 1.05 mol of triethylamine in dry toluene are added to 1 mol of the silane compound obtained in stage (A). The reaction mixture is stirred at 50° C. for 4 hours. The ammonium salt is then filtered off with suction and the filtrate is freed from the solvent by vacuum distillation. The compounds containing reactive hydrogen, of the formula (VI), used in stage (A) for the reaction of the 5 mol of dichlorodimethylsilane, the silane compounds of the formula (VIIIa) obtained in stage (A) and the compounds containing reactive hydrogen, of the formula (VII), used in stage (B) for the reaction of the chlorosilane compounds (VIIIa) are listed in the following Table 2.

TABLE 2

| Example | Compounds of the formula (VI) | Cl-silane compounds of the formula (VIIIa) obtained in stage (A) | Compound of the formula (VII) |
| --- | --- | --- | --- |
| 1 | CH$_3$O—(CH$_2$—CH$_2$—O)$_{10}$—H | Cl—Si(CH$_3$)$_2$—(O—CH$_2$—CH$_2$)$_{10}$—O—CH$_3$ | n-C$_{12}$H$_{25}$—OH |

TABLE 2-continued

| Example | Compounds of the formula (VI) | Cl-silane compounds of the formula (VIIIa) obtained in stage (A) | Compound of the formula (VII) |
|---|---|---|---|
| 2 | $CH_3O$—$(CH_2$—$CH_2$—$O)_{16}$—H | Cl—$Si(CH_3)_2$—$(O$—$CH_2$—$CH_2)_{16}$—$O$—$CH_3$ | n-$C_{12}H_{25}$—OH |
| 3 | $CH_3O$—$(CH_2$—$CH_2$—$O)_{30}$—H | Cl—$Si(CH_3)_2$—$(O$—$CH_2$—$CH_2)_{30}$—$O$—$CH_3$ | n-$C_{12}H_{25}$—OH |
| 4 | $CH_3O$—$(CH_2$—$CH_2$—$O)_{10}$—H | Cl—$Si(CH_3)_2$—$(O$—$CH_2$—$CH_2)_{10}$—$O$—$CH_3$ | n-$C_9H_{19}$—C$_6$H$_4$—OH |
| 5 | $CH_3O$—$(CH_2$—$CH_2$—$O)_{16}$—H | Cl—$Si(CH_3)_2$—$(O$—$CH_2$—$CH_2)_{16}$—$O$—$CH_3$ | n-$C_9H_{19}$—C$_6$H$_4$—OH |
| 6 | $CH_3O$—$(CH_2$—$CH_2$—$O)_{30}$—H | Cl—$Si(CH_3)_2$—$(O$—$CH_2$—$CH_2)_{30}$—$O$—$CH_3$ | n-$C_9H_{19}$—C$_6$H$_4$—OH |
| 7 | $CH_3O$—$(CH_2$—$CH_2$—$O)_{45}$—H | Cl—$Si(CH_3)_2$—$(O$—$CH_2$—$CH_2)_{45}$—$O$—$CH_3$ | n-$C_9H_{19}$—C$_6$H$_4$—OH |
| 8 | $CH_3O$—$(CH_2$—$CH_2$—$O)_{30}$—H | Cl—$Si(CH_3)_2$—$(O$—$CH_2$—$CH_2)_{30}$—$O$—$CH_3$ | n-$C_9H_{19}$—C$_6$H$_4$—O—$(CH_2CH_2$—$O)$— |
| 9 | $CH_3O$—$(CH_2$—$CH_2$—$O)_{30}$—H | Cl—$Si(CH_3)_2$—$(O$—$CH_2$—$CH_2)_{30}$—$O$—$CH_3$ | n-$C_{12}H_{25}$—$NH_2$ |

EXAMPLES 10–13

(A) Preparation of the silane derivatives of the formula (I) according to the invention in which n is 0 (general procedure)

A 50% strength by volume solution of a compound containing reactive hydrogen, of the formula (VI), in dry toluene and a solution of 1.05 mol of pyridine in 200 ml of dry toluene are added simultaneously to a 50% strength by volume solution of 1 mol of silane compound of the formula (IX) in dry toluene in a reaction vessel filled with dry nitrogen at room temperature, while stirring. The reaction mixture is heated to 70° C. and stirred at this temperature for one hour. The ammonium salt precipitate is then filtered off with suction and the filtrate is freed from the solvent in vacuo. The silane compounds of the formula (IX) used and the compounds containing active hydrogen, of the formula (VI), are listed in the following Table 3.

TABLE 3

| Example | Silane compound of the formula (IX) | Compound of the formula (VI) |
|---|---|---|
| 10 | $[n$-$C_6H_{13}]_3$Si—Cl | $CH_3O$—$(CH_2$—$CH_2$—$O)_{10}$—H |
| 11 | $[n$-$C_6H_{13}]_3$Si—Cl | $CH_3O$—$(CH_2$—$CH_2$—$O)_{16}$—H |
| 12 | $[C_6H_5]_3$Si—Cl | $CH_3O$—$(CH_2$—$CH_2$—$O)_{30}$—H |
| 13 | $[C_6H_5]_3$Si—Cl | $CH_3O$—$(CH_2$—$CH_2$—$O)_{10}$—H |

EXAMPLES 14–18

(A) Preparation of the silane derivatives of the formula (I) according to the invention, in which $R_1 = R_4 = CH_3$, m is 1 and x is —[O—$CH_2$—$CH_2$—]$_r$—O—, where r is n (general procedure)

A 20% strength by volume solution of 2.0 mol of a compound containing reactive hydrogen, of the formula (VI), in dry toluene and the solution of 2.05 mol pyridine in 200 ml of dry toluene are simultaneously added to a 20% strength by volume solution of a mixture of 0.65 mol of dichloromethylundecylsilane and 0.35 mol of dichloromethyltridecylsilane in dry toluene in a reaction vessel filled with dry nitrogen at room temperature, while stirring. The reaction mixture is heated to 70° C. and stirred at this temperature for one hour. The ammonium salt precipitate is then filtered off with suction and the filtrate is freed from the solvent in vacuo.

The dichlorosilane compounds of the formula (V) used and the compounds containing active hydrogen, of the formula (VI), are listed in the following Table 4.

TABLE 4

| Example | Dichlorosilane compound of the formula (V) | Compound of the formula (VI) |
|---|---|---|
| 14 | $CH_3$<br>$\|$<br>$C_mH_{2m+1}$Si—$Cl_2$<br>m = 11 (65%) m = 13 (35%) | $CH_3O$—$(CH_2CH_2O)_5$—H |
| 15 | $CH_3$<br>$\|$<br>$C_mH_{2m+1}$Si—$Cl_2$<br>m = 11 (65%) m = 13 (35%) | $CH_3O$—$(CH_2CH_2O)_7$—H |

TABLE 4-continued

| Example | Dichlorosilane compound of the formula (V) | Compound of the formula (VI) |
|---|---|---|
| 16 | CH$_3$<br>\|<br>C$_m$H$_{2m+1}$Si—Cl$_2$<br>m = 11 (65%) m = 13 (35%) | CH$_3$O—(CH$_2$CH$_2$O)$_{10}$—H |
| 17 | CH$_3$<br>\|<br>C$_m$H$_{2m+1}$Si—Cl$_2$<br>m = 11 (65%) m = 13 (35%) | CH$_3$O—(CH$_2$CH$_2$O)$_{16}$—H |
| 18 | CH$_3$<br>\|<br>C$_m$H$_{2m+1}$Si—Cl$_2$<br>m = 11 (65%) m = 13 (35%) | CH$_3$O—(CH$_2$CH$_2$O)$_{30}$—H |

EXAMPLE 19

(A) Determination of the emulsifier properties and of the stability of the silane derivatives according to the invention as a function of the pH of the aqueous phase of the emulsions prepared with the aid of these derivatives.

Emulsions were prepared from the following components:

Aqueous phase:
a) Aqueous buffer solution containing 50 mmol of KH$_2$PO$_4$/l; this aqueous buffer solution is brought to the desired pH by addition of HCl and NaOH;
b) Surfactant solution: This contains 6% by weight of the surfactant under investigation, dissolved in distilled water;

Hydrophobic phase:
c) Isododecane

Preparation of the emulsions:

Components (a), (b) and (c) are mixed in a volume ratio of 2:2:1 and the mixture is homogenized with a rotor-stator at 10,000 revolutions/minute for 1 minute. The 50% strength by volume oil-in-water emulsion formed contains 3% by weight of surfactant (silane derivative), based on the volume of the organic phase.

The stability of the resulting emulsion was assessed after one day and after a standing time of three weeks, the following ratings being used: Stability=I: the emulsion separates into a concentrated white upper layer (cream layer) and a milky-cloudy to clear aqueous phase in the course of a few days. The cream layer retains its white colour throughout the observation period and does not change. No formation of a separate isododecane layer takes place.

Stability=II: a cream layer forms in the course of a few hours; after one day, the cream layer has a glassy consistency (signs of droplet enlargement/coalescence). In addition, the formation of an isododecane layer on the cream layer is already detectable after one day; the volume of this isododecane layer increases in the course of the observation period.

Stability=III: the emulsion separates into an aqueous phase and into an isododecane phase in the course of a few minutes. No cream layer forms or a cream layer forms only in some parts.

The stability values obtained for the individual surfactants according to the invention at the various pH values are listed in the following Table 5.

For comparison, the stability values of two structurally related surfactants belonging to the prior art have furthermore been stated.

TABLE 5

| | Stabilities | | | | | | | |
|---|---|---|---|---|---|---|---|---|
| pH of the aqueous phase | Surfactant according to Example 1 | Surfactant A | Surfactant according to Example 3 | Surfactant B | Surfactant according to Example 6 | Surfactant according to Example 8 | Surfactant according to Example 17 | Surfactant according to Example 18 |
| 3 | III | I | III | I | III | III | III | III |
| 4 | III | I | III | I | II | II | II | II |
| 5 | III | I | III | I | I | II | I | I |
| 6 | I | I | I | I | I | I | I | I |
| 7 | I | I | I | I | I | I | I | I |
| 8 | I | I | I | I | I | I | I | I |
| 9 | I | I | I | I | I | I | I | I |
| 10 | I | I | I | I | I | I | I | |
| 11 | II | I | II | I | II | II | II | II |
| 12 | III | I | III | I | III | III | II | III |
| 13 | III | I | III | I | III | III | III | III |

Surfactants according to the prior art:

A  CH$_3$—[O—CH$_2$—CH$_2$]$_{10}$—O—C$_{10}$H$_{25}$

B  CH$_3$—[O—CH$_2$—CH$_2$]$_{30}$—O—C$_{12}$H$_{25}$

What is claimed is:

1. A process for the preparation of emulsions of other multiphase formulations comprising admixing an aqueous phase, a hydrophobic phase and a surfactant solution wherein the surfactant solution comprises a surfactant consisting essentially of a silane derivative of the formula:

$$R_1-O+CH_2-CH_2-O\!\!\mathop{]}_n\!\!\underset{\underset{R_3}{|}}{\overset{\overset{R_2}{|}}{Si}}+X\mathop{]}_m R_4, \quad (I)$$

in which
R$_1$ is H or C$_1$–C$_4$-alkyl,
n is an integer from 2 to 300,
R$_2$ and R$_3$ independently of one another are C$_1$–C$_{16}$-alkyl or phenyl,
X is —O—, —S—, —NR$_5$—(R$_5$: hydrogen or C$_1$–C$_4$-alkyl)or $$+O-CH_2-CH_2]_R O+$$

(R=integer from 1 to 100) and
m is zero or 1, and
R$_4$ is H, C$_1$–C$_{36}$-alkyl, C$_2$–C$_{36}$-alkenyl, C$_5$–C$_{36}$-cycloalkyl, C$_5$–C$_{36}$-cycloalkenyl, C$_7$–C$_{36}$-aralkyl, C$_6$–C$_{36}$-aryl, a radical of the formula (II)

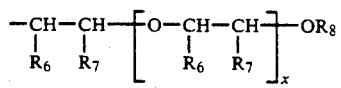 (II)

in which one of the radicals $R_6$ and $R_7$ is methyl and the other is H, $R_8$ is $C_1$–$C_4$-alkyl and x is an integer from 10 to 300, or a radical of the formula (III)

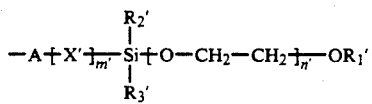 (III)

in which $R_1'$, $R_2'$, $R_3'$, $X'$, $m'$ and $n'$ have the meaning given for $R_1$, $R_2$, $R_3$, X, m and n under formula (I) and A is a 2-valent hydrophobic radical, with the proviso that the sum of the C atoms contained in the radicals $R_2$, $R_3$ and $R_4$ is at least 14.

* * * * *

UNITED STATES PATENT AND TRADEMARK OFFICE
CERTIFICATE OF CORRECTION

PATENT NO. : 5,171,476
DATED : December 15, 1992
INVENTOR(S) : Bloodworth, et al.

It is certified that error appears in the above-identified patent and that said Letters Patent is hereby corrected as shown below:

Col. 2, line 15  Delete " $[O-CH_2-CH_2]_r O]$ " and substitute -- $[O-CH_2-CH_2]_r O-$ --

Col. 4, line 12  Delete " $[O-CH_2-CH_2]_r O]$ " and substitute -- $[O-CH_2-CH_2]_r O-$ --

Col. 6, line 52  Delete " $R_1-O-[CH_2CH_2]O]_n H$ " and substitute -- $R_1-O-[CH_2CH_2-O]_n H$ --

Col. 12, line 63  Delete " $[O-CH_2-CH_2]_r O]$ " and substitute -- $[O-CH_2-CH_2]_r O-$ --

Signed and Sealed this

Fourteenth Day of June, 1994

Attest:

*Attesting Officer*

BRUCE LEHMAN

*Commissioner of Patents and Trademarks*